US007163678B2

(12) United States Patent
Norman et al.

(10) Patent No.: US 7,163,678 B2
(45) Date of Patent: Jan. 16, 2007

(54) REOVIRUS FOR THE TREATMENT OF RAL-MEDIATED CELLULAR PROLIFERATIVE DISORDERS

(75) Inventors: Kara L. Norman, Menlo Park, CA (US); Patrick W. K. Lee, Halifax (CA)

(73) Assignee: Oncolytics Biotech Inc., Calgary (CA)

( * ) Notice: Subject to any disclaimer, the term of this patent is extended or adjusted under 35 U.S.C. 154(b) by 0 days.

(21) Appl. No.: 10/704,531

(22) Filed: Nov. 6, 2003

(65) Prior Publication Data

US 2004/0146491 A1 Jul. 29, 2004

Related U.S. Application Data

(60) Provisional application No. 60/424,834, filed on Nov. 7, 2002.

(51) Int. Cl.
*A01N 63/00* (2006.01)
*A61K 39/15* (2006.01)
*C12N 15/00* (2006.01)

(52) U.S. Cl. .................. 424/93.1; 424/93.2; 424/215.1

(58) Field of Classification Search ............... 424/93.2, 424/93.6, 215.1, 93.1; 514/44
See application file for complete search history.

(56) References Cited

U.S. PATENT DOCUMENTS

| 5,023,252 | A | | 6/1991 | Hseih | |
|---|---|---|---|---|---|
| 6,110,461 | A | * | 8/2000 | Lee et al. | 424/93.6 |
| 6,136,307 | A | * | 10/2000 | Lee et al. | 424/93.6 |
| 6,261,555 | B1 | * | 7/2001 | Lee et al. | 424/93.6 |
| 6,344,195 | B1 | * | 2/2002 | Lee et al. | 424/93.6 |
| 6,455,038 | B1 | * | 9/2002 | Lee et al. | 424/93.6 |
| 6,565,831 | B1 | * | 5/2003 | Coffey et al. | 424/1.33 |
| 6,811,775 | B1 | * | 11/2004 | Lee et al. | 424/93.6 |
| 2002/0187125 | A1 | * | 12/2002 | Lee et al. | |
| 2003/0003080 | A1 | * | 1/2003 | Lee et al. | |
| 2004/0265271 | A1 | * | 12/2004 | Lee et al. | |

FOREIGN PATENT DOCUMENTS

WO WO 9908692 A1 * 2/1999

OTHER PUBLICATIONS

Hamad et al. Genes & Development 2002, vol. 16, pp. 2045-2057.*
Urano et al. The EMBO Journal 1996, vol. 15, No. 4, pp. 810-818,*
Strong et al. The EMBO Journal 1998, vol. 17, No. 12, pp. 3351-3362.*
Hirasawa et al. Cancer Research 2002, vol. 62, pp. 1696-1701.*
Hofer et al. Brief. Comminucation 1998, pp. 839-842 plus S1-S2.*
Norman et al. PNAS Jul. 2004, vol. 10, No. 30, pp. 11099-11104.*
Aronheim, A. et al. (1994). Membrane targeting of the nucleotide exchange factor Sos is sufficient for activating the Ras signaling Pathway. *Cell* 78:949-961.
Barbacid, M. (1987). *Annu. Rev. Biochem.* 56:779-827.
Berrozpe, G. et al. (1994). Comparative analysis of Mutations in the p53 and K-ras genes. *Int. J. Cancer* 58:185-191.
Bischoff, J.R. and Samuel, C.E. (1989). Mechanism of interferon action: activation of the human P1/eIF-2α protein kinase by individual reovirus s-class mRNAs: s1 mRNA is a potent activator relative to s4 mRNA. *Virology* 172:106-115.
Bos, J.L. (1989). ras Oncogenes in human cancer: a review. *Cancer Res.* 49:4682-4689.
Bos, J.L. (1998). All in the family? New insights and questions regarding interconnectivity of Ras, Rap1 and Ral. *EMBO J.* 17:6776-6782.
Cahill, M.A. et al. (1996). Signalling pathways. Jack of all cascades. *Curr. Biol.* 6:16-19.
Chandran, K. and Nibert M.L. (1998). Protease cleavage of reovirus capsid protein μ1/μ1C is blocked by alkyl sulfate detergents, yielding a new type of infectious subvirion particle. *J. Virol.* 72:467-475.
Chaubert, P. et al. (1994). K-ras mutations and p53 alterations in neoplastic and nonneoplastic lesions associated with longstanding ulcerative colitis. *Am. J. Path.* 144:767-775.
Cuff, C.F. et al. (1998). Enteric reovirus infection as a probe to study immunotoxicity of the gastrointestinal tract. *Toxicological Sciences* 42:99-108.

(Continued)

*Primary Examiner*—Bruce R. Campell
*Assistant Examiner*—Bao Qun Li
(74) *Attorney, Agent, or Firm*—Fish & Richardson P.C.

(57) ABSTRACT

Methods for treating proliferative disorders, by administering reovirus to a ral-mediated proliferative disorder, are disclosed. The reovirus is administered so that it ultimately directly contacts target cancer cells. Proliferative disorders include but are not limited to neoplasms. Human reovirus, non-human mammalian reovirus, and/or avian reovirus can be used. If the reovirus is human reovirus, serotype 1 (e.g., strain Lang), serotype 2 (e.g., strain Jones), serotype 3 (e.g., strain Dearing or strain Abney), other serotypes or strains of reovirus, and recombinant reovirus can be used. Combinations of more than one type and/or strain of reovirus can be used, as can reovirus from different species of animal. Either solid neoplasms or hematopoietic neoplasms can be treated.

31 Claims, No Drawings

OTHER PUBLICATIONS de Ruiter, N.D. et al. (2000). Ras-dependent regulation of c-Jun phosphorylation is mediated by the Ral guanine nucleotide exchange factor-Ral pathway. *Mol. Cell Biol.* 20:8480-88.

Der, S.D. et al. (1997). A double-stranded RNA-activated protein kinase-dependent pathway mediating stress-induced apoptosis. *Proc. Natl. Acad. Sci. U.S.A.* 94:3279-3283.

Dudley, D.T. et al. (1995). A synthetic inhibitor of the mitogen-activated protein kinase cascase. *Proc. Natl. Acad. Sci. U.S.A.* 92:7686-7689.

Duncan, R. et al. (1991). Conformational and functional analysis of the C-terminal globular head of the reovirus cell attachment protein. *Virology* 182:810-819.

Helbing, C.C. et al. (1997). A novel candidate tumor suppressor, ING1, is involved in the regulation of apoptosis. *Cancer Res.* 57:1255-1258.

Hirasawa, K. et al. (2002). Oncolytic reovirus against ovarian and colon cancer. *Cancer Research* 62:1696-1701.

Hu, Y. and Conway, T.W. (1993), 2-aminopurine inhibits the double-stranded RNA-dependent protein kinase both *in vitro* and *in vivo*. *J. Interferon Res.* 13:323-328.

Janes, P.W. et al. (1994). Activation of the Ras signalling pathway in human breast cancer cells overexpressing *erb*B-2. *Oncogene* 9:3601-3608.

Laemmli, U.K. (1970). Cleavage of structural proteins during the assembly of the head of bacteriophage T4. *Nature* 227:680-685.

Lee, J.M. et al. (1993). p53 mutations increase resistance to ionizing radiation. *Proc. Natl. Acad. Sci. U.S.A.* 90:5742-5746.

Lee, P.W.K. et al. (1981). Characterization of anti-reovirus immunoglobulins secreted by cloned hybridoma cell lines. *Virology* 108:134-146.

Levitzki, A. (1994). Signal-transduction therapy: a novel approach to disease management. *Eur. J. Biochem.* 226:1-13.

Lowe, S.W. et al. (1994). p53 status and the efficacy of cancer therapy *in vivo*. *Science* 266:807-810.

Mah, D.C. et al. (1990). The N-terminal quarter of reovirus cell attachment protein $\delta$1 possesses intrinsic virion-anchoring function. *Virology* 179:95-103.

McCrae, M.A. and Joklik, W.K. (1978). The nature of the polypeptide encoded by each of the 10 double-stranded RNA segments of reovirus type 3. *Virology* 89:578-593.

Mills, N.E. et al. (1995). Increased prevalence of K-ras oncogene mutations in lung adenocarcinoma. *Cancer Res.* 55:1444-1447.

Mundschau, L.J. and Faller, D.V. (1992). Oncogenic *ras* induces an inhibitor of double-stranded RNA-dependent eukaryotic initiation factor $2\alpha$-kinase activation. *J. Biol. Chem.* 267:23092-98.

Nagata, L. et al. (1984). Molecular cloning and sequencing of the reovirus (serotype 3) S1 gene which encodes the viral cell attachment protein $\delta$1. *Nucleic Acids Res.* 12:8699-8710.

Nedergaard, T. et al. (1997). A one-step DGGE scanning method for detection of mutations in the K-,N-, and H-ras oncogenes: mutations at codons 12,13 and 61 are rare in B-cell non-Hodgkin's lymphoma. *Int. J. Cancer.* 71:364-9.

Nibert, M.L., et al., (1996). Reoviruses and their replication. *Fields Virology*, 3$^{rd}$ Edition, Lippincott-Raven Publishers, pp. 1557-1596.

Raybaud-Diogene, H. et al. (1997). Markers of radioresistance in squamous cell carcinomas of the head and neck: a clinicopathologic and immunohistochemical study. *J. Clin. Oncology*, 15:1030-1038.

Robinson, M.J. and Cobb, M.H. (1997). Mitogen-activated protein kinase pathways. *Curr. Opin. Cell. Biol.* 9:180-186.

Rosen, L. (1960). Serologic grouping of reoviruses by hemagglutination-inhibition. *Am. J. Hyg.* 71:242-249.

Sabin, A.B. (1959). Science in the news. *Science* 130:966-972.

Samuel, C.E. and Brody, M.S. (1990). Biosynthesis of reovirus-specified polypeptides. *Virology* 176:106-113.

Smith, R.E. et al. (1969). Polypeptide components of virions, top component and cores of reovirus type 3. *Virology* 39:791-810.

Stanley, N.F. (1967). Reoviruses. *Br. Med. Bull.* 23:150-154.

Strong, J.E. et al. (1993). Evidence that the epidermal growth factor receptor on host cells confers reovirus infection efficiency. *Virology* 197:405-411.

Strong, J.E. amd Lee, P.W.K. (1996). The *v-erb*B oncogene confers enhanced cellular susceptibility to reovirus infection. *J. Virol.* 70:612-616.

Trimble, W.S. et al. (1986). Inducible cellular transformation by a metallothionein-*ras* hybrid oncogene leads to natural killer cell susceptibility. *Nature* 321:782-784.

Turner, D.L. et al. (1992) Site directed mutagenesis of the C-terminal portion of reovirus protein $\delta$1 evidence for a conformation-dependent receptor binding domain. *Virology* 186:219-227.

Tweeddale, M.E. et al. (1987). The presence of clonogenic cells in high-grade malignant lymphoma: a prognostic factor. *Blood* 69:1307-1.

Vojtek, A.B. amd Der, C.J.. (1998). Increasing complexity of the Ras signaling pathway. *J. Biol. Chem.* 273:19925-28.

Ward, Y.. et al. (2001). Signal pathways which promote invasion and metastasis: critical and distinct contributions of extracellular signal-regulated kinase and Ral-specific guanine exchange factor pathways. *Mol. Cell Biol.* 21:5958-69.

Waters, S.D. et al. (1995). Desensitization of Ras activation by a feedback disassociation of the Sos-Grb2 complex. *J. Biol. Chem.* 270-20883-20886.

Wiesmüller, L. and Wittinghofer, F. (1994). Signal transduction pathways involving ras mini review. *Cellular Signaling* 6:247-267.

Wong, H. et al. (1994). Monitoring mRNA expression by polymerase chain reaction: the "primer-dropping" method. *Anal. Biochem.* 223:251-258.

Yamamoto, T, et al. (1999). Ras-induced transformation and signaling pathway. *J. Biochem.* (Tokyo) 126(4):799-803.

Yang, Y.L. et al. (1995). Deficient signaling in mice devoid of double-stranded RNA-dependent protein kinase. *EMBO J.* 14:6095-6106.

Yu, D. et al. (1996). Overexpression of *c-erb*B-2/*neu* in breast cancer cells confers increased resistance to Taxol via *mdr*-1-independent mechanisms. *Oncogene* 13:1359-1365.

* cited by examiner

US 7,163,678 B2

REOVIRUS FOR THE TREATMENT OF RAL-MEDIATED CELLULAR PROLIFERATIVE DISORDERS

RELATED APPLICATION

This application claims the benefit of U.S. Provisional Application No. 60/424,834, filed Nov. 7, 2002.

FIELD OF THE INVENTION

The present invention pertains to methods for treating ral-mediated cell proliferative disorders in an animal using reovirus.

REFERENCES

The following publications, patent applications and patents are cited in this application:
U.S. Pat. No. 5,023,252;
U.S. Pat. No. 6,136,307;
Aronheim, A. et al. (1994) Cell 78:949–961;
Barbacid, M. (1987) Annu. Rev. Biochem. 56:779–827;
Berrozpe, G. et al. (1994) Int. J. Cancer, 58:185–191;
Bischoff, J. R. and Samuel, C. E. (1989) Virology 172:106–115;
Bos, J. (1989) Cancer Res. 49:4682;
Bos, J. L. (1998) All in the family? New insights and questions regarding interconnectivity of Ras, Rap1 and Ral. EMBO J. 17:6776–6782;
Cahill, M. A. et al. (1996) Curr. Biol. 6:16–19;
Chandran, K and Nibert, M. L. (1998) Protease cleavage of reovirus capsid protein mul/mulC is blocked by alkyl sulfate detergents, yielding a new type of infectious subvirion particle. J. Virol. 72:467–75;
Chaubert, P. et al. (1994) Am. J. Path. 144:767;
Cuff, C. F. et al. (1998) Enteric reovirus infection as a probe to study immunotoxicity of the gastrointestinal tract. Toxicological Sciences 42:99–108;
de Ruiter, N. D. et al. (2000) Ras-dependent regulation of c-Jun phosphorylation is mediated by the Ral guanine nucleotide exchange factor-Ral pathway. Mol. Cell Biol. 20:8480–88;
Der, S. D. et al. (1997) Proc. Natl. Acad. Sci. U.S.A. 94:3279–3283;
Dudley, D. T. et al. (1995) Proc. Natl. Acad. Sci. U.S.A. 92:7686–7689;
Duncan, R. et al. (1991) Conformational and functional analysis of the C-terminal globular head of the reovirus cell attachment protein. Virology 182:810–9;
Fields, B. N. et al. (1996) Fundamental Virology, 3rd Edition, Lippincott-Raven;
Harlow, E. and Lane, D. (1988) "Antibodies: A laboratory manual", Cold Spring Harbor Laboratory;
Helbing, C. C. et al. (1997) Cancer Res. 57:1255–1258;
Hirasawa, K. et al. (2002) Oncolytic reovirus against ovarian and colon cancer. Cancer Research 62:1696–1701;
Hu, Y. and Conway, T. W. (1993) J. Interferon Res. 13:323–328;
James, P. W. et al. (1994) Oncogene 9:3601;
Laemmli, U. K. (1970) Nature 227:680–685;
Lee, J. M. et al. (1993) Proc. Natl. Acad. Sci. U.S.A. 90:5742–5746;
Lee, P. W. K. et al. (1981) Virology 108:134–146;
Levitzki, A. (1994) Eur. J. Biochem. 226:1;
Lowe, S. W. et al. (1994) Science 266:807–810;
Lyon, H. (1994) Cell Biology, A Laboratory Handbook, J. E. Celis, ed., Academic Press, p. 232;
Mah, D. C. et al. (1990) The N-terminal quarter of reovirus cell attachment protein sigma 1 possesses intrinsic virion-anchoring function. Virology 179:95–103;
McRae, M. A. and Joklik, W. K. (1978) Virology 89:578–593;
Millis, N E et al. (1995) Cancer Res. 55:1444;
Mundschau, L. J. and Faller, D. V. (1992) J. Biol. Chem. 267:23092–23098;
Nagata, L. et al. (1984) Nucleic Acids Res. 12:8699–8710;
Nedergaard, T. et al. (1997) A one-step DGGE scanning method for detection of mutations in the K-, N-, and H-ras oncogenes: mutations at codons 12, 13 and 61 are rare in B-cell 2non-Hodgkin's lymphoma. Int. J. Cancer. 71:364–9;
Nibert, M. L., Schiff, L. A., and Fields, B. N., Reoviruses and their replication in Fields Virology, $3^{rd}$ Edition, Lippencott-Raven Press, 1995, pp. 1557–96;
Raybaud-Diogene. H. et al. (1997) J. Clin. Oncology, 15:1030–1038;
Remington's Pharmaceutical Sciences, Mace Publishing Company, Philadelphia Pa. $17^{th}$ ed. (1985);
Robinson, M. J. and Cobb, M. H. (1997) Curr. Opin. Cell. Biol. 9:180–186;
Rosen, L. (1960) Am. J. Hyg. 71:242;
Sabin, A. B. (1959) Science 130:966;
Samuel, C. E. and Brody, M. (1990) Virology 176:106–113;
Smith, R. E. et al. (1969) Virology 39:791–800;
Stanley, N. F. (1967) Br. Med. Bull. 23:150;
Strong, J. E. et al. (1993) Virology 197:405–411;
Strong, J. E. and Lee, P. W. K. (1996) J. Virol. 70:612–616;
Trimble, W. S. et al. (1986) Nature 321:782–784;
Turner, D. L. et al. (1992) Site directed mutagenesis of the C-terminal portion of reovirus protein sigmal:evidence for a conformation-dependent receptor binding domain. Virology 186:219–27;
Tweeddale, M. E. et al. (1987) The presence of clonogenic cells in high-grade malignant lymphoma: a prognostic factor. Blood 69:1307–14;
Vojtek, A. B. and Der, C. J. (1998) Increasing complexity of the Ras signaling pathway. J. Biol. Chem. 273:19925–28;
Ward, Y. et al. (2001) Signal pathways which promote invasion and metastasis: critical and distinct contributions of extracellular signal-regulated kinase and Ral-specific guanine exchange factor pathways. Mol. Cell Biol. 21:5958–69;
Waters, S. D. et al. (1995) J. Biol. Chem. 270:20883–20886;
Wiessmuller, L. and Wittinghofer, F. (1994) Cellular Signaling 6:247–267;
Wong, H. et al. (1994) Anal. Biochem. 223:251–258;
Yamamoto, T. et al. (1999) Ras-induced transformation and signaling pathway. J. Biochem. (Tokyo) 126:799–803;
Yang, Y. L. et al. (1995) EMBO J. 14:6095–6106;
Yu, D. et al. (1996) Oncogene 13:1359.

All of the above publications, patent applications and patents are herein incorporated by reference in their entirety to the same extent as if each individual publication, patent application or patent was specifically and individually indicated to be incorporated by reference in its entirety.

STATE OF THE ART

Normal cell proliferation is regulated by a balance between growth-promoting proto-oncogenes and growth-constraining tumor-suppressor genes. Tumorigenesis can be caused by genetic alterations to the genome that result in the mutation of those cellular elements that govern the interpretation of cellular signals, such as potentiation of proto-oncogene activity or inactivation of tumor suppression. It is believed that the interpretation of these signals ultimately influences the growth and differentiation of a cell, and that misinterpretation of these signals can result in neoplastic growth (neoplasia).

Genetic alteration of the proto-oncogene Ras is believed to contribute to approximately 30% of all human tumors [Wiessmuller and Wittinghofer (1994); Barbacid (1987)]. The role that Ras plays in the pathogenesis of human tumors is specific to the type of tumor. Activating mutations in Ras itself are found in most types of human malignancies, and are highly represented in pancreatic cancer (80%), sporadic colorectal carcinomas (40–50%), human lung adenocarcinomas (15–24%), thyroid tumors (50%) and myeloid leukemia (30%) [Millis et al. (1995); Chaubert et al. (1994); Bos (1989)]. Ras activation is also demonstrated by upstream mitogenic signaling elements, notably by tyrosine receptor kinases (RTKs). These upstream elements, if amplified or overexpressed, ultimately result in elevated Ras activity by the signal transduction activity of Ras. Examples of this include overexpression of PDGFR in certain forms of glioblastomas, as well as in c-erbB-2/neu in breast cancer [Levitzki (1994); James et al. (1994); Bos (1989)].

Mutations in downstream effectors in the ras pathway may also contribute to cell transformation or cause cell transformation in the absence of ras mutations. In particular, studies have shown that mutations in the ral pathway may are sufficient to cause cell transformation [Ward et al. (2001); de Ruiter et al. (2000); Bos (1998); and references within].

Cell proliferative disorders are mainly treated by conventional therapies including surgery, chemotherapy, and radiation. Surgery is typically used as the primary treatment for early stages of cancer; however, many tumors cannot be completely removed by surgical means. In addition, metastatic growth of neoplasms may prevent complete cure of cancer by surgery. Chemotherapy involves administration of compounds having antitumor activity, such as alkylating agents, antimetabolites, and antitumor antibiotics. The efficacy of chemotherapy is often limited by severe side effects, including nausea and vomiting, bone marrow depression, renal damage, and central nervous system depression. Radiation therapy relies on the greater ability of normal cells, in contrast with neoplastic cells, to repair themselves after treatment with radiation. Radiotherapy cannot be used to treat many neoplasms, however, because of the sensitivity of tissue surrounding the tumor. In addition, certain tumors have demonstrated resistance to radiotherapy and such may be dependent on oncogene or anti-oncogene status of the cell [Lee et al. (1993); Lowe et al. (1994); Raybaud-Diogene et al. (1997)]. In view of the drawbacks associated with the current means for treating neoplastic growth, the need still exists for improved methods for the treatment of neoplasms.

SUMMARY OF THE INVENTION

The present invention pertains to a method of treating a ral-mediated proliferative disorder in an animal, comprising administering to the proliferating cells in an animal an effective amount of one or more reoviruses under conditions which result in substantial lysis of the proliferating cells.

In one embodiment of the invention, the cell proliferative disorder is a neoplasm, including but not limited to, lung cancer, prostate cancer, colorectal cancer, thyroid cancer, renal cancer, adrenal cancer, liver cancer, pancreatic cancer, breast cancer, or central or peripheral nervous system cancer. In another embodiment, the neoplasm is a hematopoietic neoplasm. In another embodiment, the neoplasm is a solid neoplasm. In yet another embodiment, the disorder is neurofibromatosis. The neoplasm may be metastatic.

In one embodiment of the invention, a single mammalian or avian reovirus is used. In another embodiment, more than one type or strain of reovirus is used. A human reovirus may be used, for example, serotype 1 reovirus (Lang), serotype 2 reovirus (Jones), or serotype 3 reovirus (Dearing or Abney). The reovirus may also be one or more field isolates from one or more species, including but not limited to avian and mammalian species.

In another embodiment of the invention, the reovirus is one or more recombinant reoviruses. The recombinant reovirus may be from two or more strains of reovirus. The recombinant reovirus may be naturally-occurring or non-naturally-occurring. The recombinant reovirus may comprises naturally-occurring variant coat protein coding sequences or mutated coat protein coding sequences. In one embodiment, the recombinant reovirus results from reassortment of reoviruses selected from the group consisting of serotype 1 reovirus, serotype 2 reovirus, and serotype 3 reovirus. The recombinant reovirus may be generated by co-infection of mammalian cells with different subtypes of reovirus.

In one embodiment of the invention, approximately 1 to approximately $10^{15}$ plaque forming units (pfu) of reovirus/kg body weight are administered. The reovirus may be administered in a single dose or in more than one dose. The invention also contemplates a number of routes of administration for the invention. In one embodiment, the reovirus is administered by injection into or near the solid neoplasm. In another embodiment, the reovirus is administered, for example, intravascularly, intrathecally, intravenously, intramuscularly, subcutaneously, intraperitoneally, topically, orally, rectally, vaginally, nasally, or intratumorally. More than one route of administration may be used to deliver reovirus. In another embodiment, reovirus is administered along with an effective amount of a chemotherapeutic agent. The chemotherapeutic agent is preferably not BCNU. The invention further includes the use of an appropriate immunosuppressive composition in combination with any reoviruses described herein.

In one embodiment of the invention, the animal to which reovirus is administered is immunocompetent. The reovirus may be immunoprotected or encapsulated in a micelle. In addition, any reovirus or combination of reoviruses described herein may be otherwise chemically or genetically modified; for example, the reovirus may be treated with a protease prior to administration.

The present invention pertains to a method of treating a ral-mediated proliferative disorder comprising suppressing or otherwise inhibiting the immune system of the mammal and, concurrently or subsequently, administering to the proliferating cells an effective amount of one or more reoviruses under conditions which result in substantial lysis of the proliferating cells. Alternatively, reovirus may be administered to a mammal with a diminished immune response system under conditions which result in substantial lysis of the proliferating cells. Immune systems may be compromised by one or more of the following: an HIV infection; as a side effect of chemotherapy or radiation therapy; by selective removal of B and/or T cell populations; by removal of antibodies (anti-antireovirus antibodies or all antibodies), and the like. In another embodiment, the reovirus is administered along with an effective amount of an anti-antireovirus antibody.

The immunosuppression or immunoinhibition may be accomplished by means of an immunosuppressant, an immune suppressive agent, or by any other means which inhibits a mammal's immune system or renders the mammal immunodeficient. When an immunosuppressant is used, it is preferably administered prior to or concurrent with reovirus administration. The mammal may be rendered immunosuppressed, immunodeficient or immunoinhibited prior to or concurrent with reovirus administration.

The invention also provides pharmaceutical compositions comprising any reovirus or combination of reovirus described above along with a pharmaceutically acceptable excipient. The pharmaceutical composition may further comprise an immunostimulatory agent. The methods and pharmaceutical compositons of the invention provide an effective means to treat neoplasia, without the side effects associated with other forms of cancer therapy. Furthermore, because reovirus is not known to be associated with a disease, any safety concerns associated with deliberate administration of a virus are minimized.

The foregoing and other objects, features and advantages of the invention will be apparent from the following more particular description of preferred embodiments of the invention.

DETAILED DESCRIPTION OF THE INVENTION

The invention pertains to methods of treating a ral-mediated cell proliferative disorder, in an animal, by administering reovirus to the proliferating cells.

The name reovirus (Respiratory and enteric orphan virus) is a descriptive acronym suggesting that these viruses, although not associated with any known disease state in humans, can be isolated from both the respiratory and enteric tracts [Sabin (1959)]. The term "reovirus" refers to all viruses classified in the reovirus genus.

Reoviruses are viruses with a double-stranded, segmented RNA genome. The virions measure 60–80 nm in diameter and possess two concentric capsid shells, each of which is icosahedral. The genome consists of double-stranded RNA in 10–12 discrete segments with a total genome size of 16–27 kbp. The individual RNA segments vary in size. Three distinct but related types of reovirus have been recovered from many species. All three types share a common complement-fixing antigen.

The human reovirus consists of three serotypes: type 1 (strain Lang or T1L), type 2 (strain Jones, T2J), and type 3 (strain Dearing or strain Abney, T3D). The three serotypes are easily identifiable on the basis of neutralization and hemagglutinin-inhibition assays [Sabin (1959); Fields et al. (1996); Rosen (1960); Stanley (1967)].

Although reovirus is not known to be associated with any particular disease, many people have been exposed to reovirus by the time they reach adulthood (i.e., fewer than 25% in children <5 years old, to greater than 50% in those 20–30 years old [Jackson and Muldoon (1973); Stanley (1974)]. Reovirus binds efficiently to a multitude of cell lines and as such can potentially target many different tissues; however, there are significant differences in susceptibility to reovirus infection between cell lines.

As described in U.S. Pat. No. 6,136,307, herein incorporated by reference in its entirety, it has been discovered that cells which are resistant to reovirus infection became susceptible to reovirus infection when transformed by a gene in the Ras pathway. "Resistance" of cells to reovirus infection indicates that infection of the cells with the virus did not result in significant viral production or yield. Cells that are "susceptible" are those that demonstrate induction of cytopathic effects, viral protein synthesis, and/or virus production. Resistance to reovirus infection was found to be at the level of gene translation, rather than at early transcription: while viral transcripts were produced, virus proteins were not expressed. Without being limited to a theory, it is thought that viral gene transcription in resistant cells correlated with phosphorylation of an approximately 65 kDa cell protein, determined to be double-stranded RNA-activated protein kinase (PKR), that was not observed in transformed cells. Phosphorylation of PKR lead to inhibition of translation. When phosphorylation was suppressed by 2-aminopurine, a known inhibitor of PKR, drastic enhancement of reovirus protein synthesis occurred in the untransformed cells. Furthermore, a severe combined immunodeficiency (SCID) mouse model in which tumors were created on both the right and left hind flanks revealed that reovirus significantly reduced tumor size when injected directly into the right-side tumor; in addition, significant reduction in tumor size was also noted on the left-side tumor which was not directly injected with reovirus, indicating that the oncolytic capacity of the reovirus was systemic as well as local.

These results indicated that reovirus uses the host cell's Ras pathway machinery to downregulate PKR, thereby usurping the host cell Ras signaling pathway to facilitate virus replication. For both untransformed (reovirus-resistant) and EGFR-, Sos-, or ras-transformed (reovirus-susceptible) cells, virus binding, internalization, uncoating, and early transcription of viral genes all proceed normally. In the case of untransformed cells, secondary structures on the early viral transcripts inevitably trigger the phosphorylation of PKR, thereby activating it, leading to the phosphorylation of the translation initiation factor eIF-2α, and hence the inhibition of viral gene translation. In the case of EGFR-, Sos-, or ras-transformed cells, the PKR phosphorylation step is prevented or reversed by Ras or one of its downstream elements, thereby allowing viral gene translation to ensue. The action of Ras (or a downstream element) can be mimicked by the use of 2-aminopurine (2-AP), which promotes viral gene translation (and hence reovirus infection) in untransformed cells by blocking PKR phosphorylation.

Ras is known to interact with a number of downstream effectors, including members of the Raf family (e.g., Raf1, B-raf, and A-raf), members of the RalGEF family (e.g., RalGDS, RGL1, RGL2, and Rlf), and phosphotidylinositol-3-kinases (PI-3 kinases) (e.g., isoforms of protein kinase C, AKT kinase/protein kinase B, p70-S6 kinase, and RacGEFs). The availability of Ras variants that are selectively defective in their ability to interact with downstream effectors has permitted the determination of which effectors are involved in Ras-dependent cell transformation. For example, RasV12S35 and RasV12E38 only activate Raf, RasV12G37 only activates RalGEF, and RasV12C40 only activates PI-3 kinase. Evidence obtained using cells harboring such Ras variants indicates that activation of the Ral pathway is important for the abnormal growth phenotype of cells harboring mutated ras genes.

Moreover, experimental evidence suggests that activation of the Ral pathway may be sufficient to cause cell transformation in the absence of accompanying mutations in the ras gene [Ward et al. (2001); de Ruiter et al. (2000); Bos (1998); and references within]. For example, it is well known that cells harboring activated Ras produce elevated amounts of phosphorylated c-Jun. c-Jun is a transcription factor required for normal cell development but is also associated with uncontrolled cell proliferation in its phosphorylated form. However, cells harboring normal Ras along with Rlf, an activated form of RalGEF, also produce elevated amounts of phosphorylated c-Jun, suggesting that cell proliferation can occur independent of ras mutations [de Ruiter et al. (2000)]. Other studies have suggested that while activated ral may contribute to the phenotype normally associated with mutations in the ras gene, and dominant-negative ral can block transformation mediated by ras mutations, activated ral is less efficient than activated ras in inducing cell transformation [Yamamoto et al. (1999); and references within]. These observation are consistent with a role for other ras effectors, in addition to ral, in contributing to the abnormal growth phenotype associated with ras mutations. The Ral family has also been implicated in the regulation o phospholipase C and rearrangement of the actin cytoskeleton [Vojtek and Der (1998); and references within].

Thus, reovirus can be used to selectively lyse cells with an activated ras pathway that proliferate abnormally rapidly. Such cells may have a mutation in the ras gene itself, or any upstream or downstream element in the ras pathway. Since there are several downstream pathways that can be activated by ras, it was not clear, prior to the present invention, which downstream pathways are associated with reovirus susceptibility.

The instant invention is based, in part, on Applicant's discovery that reovirus is also capable of infecting transformed cells that are either known to harbor, or are likely to harbor, normal forms of ras but mutated signaling molecules involved in the ral pathway. In some cases, the susceptible cells showed elevated levels of ras activity, despite possessing a normal ras gene, presumably the result of activated pathways upstream of ras. In other cases, susceptible cells harbored mutated ras downstream effectors. Additionally, experimental data suggested that specific inhibition of the ral pathway in ras-transformed cells caused cells that were normally susceptible to reovirus infection to become resistant to infection.

Taken together, these data strongly support a model in which reovirus susceptibility is mediated by a pathway downstream of ras, such as the ral pathway. The instant invention includes the use of reovirus to infect and cause oncolysis of cells that proliferate uncontrollably as a result of ral-associated acquired or genetic defects. Of particular interest are cells with defects in the ral pathway. The methods of the instant invention also include administering reovirus to cells or masses of cells with proliferative defects that are not the result of mutations in the ras gene.

Various reoviruses can be used to practice the invention. Representative types of human reovirus include type 1 (e.g., strain Lang or T1L); type 2 (e.g., strain Jones or T2J); and type 3 (e.g., strain Dearing or strain Abney, T3D or T3A). In a preferred embodiment, the reovirus is human reovirus serotype 3. More preferably the reovirus is human reovirus serotype 3, strain Dearing. Alternatively, the reovirus can be a non-human mammalian reovirus (e.g.,a non-human primate reovirus, such as baboon; equine; or canine reovirus) or a non-mammalian reovirus (e.g., avian reovirus). A combination of different serotypes and/or different strains of reovirus, such as reovirus from different species of animal, can be used.

The reovirus may be naturally occurring or modified. The reovirus is "naturally-occurring" when it can be isolated from a source in nature and has not been intentionally modified by humans in the laboratory. For example, the reovirus can be from a "field source," e.g., a human patient.

The reovirus may be modified but still capable of lytically infecting an animal cell having an activated ras pathway. The reovirus may be chemically or biochemically pretreated (e.g., by treatment with a protease, such as chymotrypsin or trypsin) prior to administration to the proliferating cells. Pretreatment with a protease removes the outer coat or capsid of the virus and may increase the infectivity of the virus. The reovirus may be coated in a liposome or micelle [Chandran and Nibert (1998)] to reduce or prevent an immune response from a mammal which has developed immunity to the reovirus. For example, the virion may be treated with chymotrypsin in the presence of micelle forming concentrations of alkyl sulfate detergents to generate a new infectious subvirion particle.

The reovirus may be a recombinant reovirus resulting from the recombination/reassortment of genomic segments from two or more genetically distinct reoviruses. Recombination/reassortment of reovirus genomic segments may occur in nature following infection of a host organism with at least two genetically distinct reoviruses. Recombinant virions can also be generated in cell culture, for example, by co-infection of permissive host cells with genetically distinct reoviruses [Nibert et al. 1995)].

Accordingly, the invention contemplates the use of recombinant reovirus resulting from reassortment of genome segments from two or more genetically distinct reoviruses, including but not limited to, human reovirus, such as type 1 (e.g., strain Lang), type 2 (e.g., strain Jones), and type 3 (e.g., strain Dearing or strain Abney), non-human mammalian reoviruses, or avian reovirus. The invention further contemplates the use of recombinant reoviruses resulting from reassortment of genome segments from two or more genetically distinct reoviruses wherein at least one parental virus is genetically engineered, comprises one or more chemically synthesized genomic segment, has been treated with chemical or physical mutagens, or is itself the result of a recombination event. The invention further contemplates the use of recombinant reovirus that have undergone recombination in the presence of chemical mutagens, including but not limited to dimethyl sulfate and ethidium bromide, or physical mutagens, including but not limited to ultraviolet light and other forms of radiation.

The invention further contemplates the use of recombinant viruses that comprise deletions or duplications in one or more genome segments, that comprise additional genetic information as a result of recombination with a host cell genome, or that comprise synthetic genes.

The reovirus may be modified by incorporation of mutated coat proteins, such as for example, into the virion outer capsid. The proteins may be mutated by replacement, insertion or deletion. Replacement includes the insertion of different amino acids in place of the native amino acids. Insertions include the insertion of additional amino acid residues into the protein at one or more locations. Deletions include deletions of one or more amino acid residues in the protein. Such mutations may be generated by methods known in the art. For example, oligonucleotide site directed mutagenesis of the gene encoding for one of the coat proteins could result in the generation of the desired mutant coat protein. Expression of the mutated protein in reovirus infected mammalian cells in vitro such as COS1 cells will result in the incorporation of the mutated protein into the reovirus virion particle (Turner et al. (1992); Duncan et al. (1991); Mah et al. (1990)].

The reovirus is preferably a reovirus modified to reduce or eliminate an immune reaction to the reovirus. Such a modified reovirus is termed an "immunoprotected reovirus". The modifications could include packaging of the reovirus in a liposome, a micelle or other vehicle to mask the reovirus from the host immune system. Alternatively, the outer capsid of the reovirus virion particle may be removed since the proteins present in the outer capsid are the major determinant of the host humoral and cellular responses. In addition to reducing or eliminating immune responses, the modifications may also reduce non-specific uptake of the virus in normal tissues. As discussed above, reovirus is capable of binding to a multitude of cell types, presumably due to the ubiquitous nature of its receptor. Therefore, by masking the reovirus, non-specific binding and uptake can be reduced.

A "proliferative disorder" is any cellular disorder in which the cells proliferate more rapidly than normal tissue growth. Thus a "proliferating cell" is a cell that is proliferating more rapidly than normal cells. The proliferative disorder, includes but is not limited to neoplasms. A neoplasm is an abnormal tissue growth, generally forming a distinct mass, that grows by cellular proliferation more rapidly than normal tissue growth. Neoplasms show partial or total lack of structural organization and functional coordination with normal tissue. These can be broadly classified into three major types. Malignant neoplasms arising from epithelial structures are called carcinomas, malignant neoplasms that originate from connective tissues such as muscle, cartilage, fat or bone are called sarcomas and malignant tumors affecting hematopoetic structures (structures pertaining to the formation of blood cells) including components of the immune system, are called leukemias and lymphomas. A tumor is the neoplastic growth of the disease cancer. As used herein, a "neoplasm", also referred to as a "tumor", is intended to encompass hematopoietic neoplasms as well as solid neoplasms. Other proliferative disorders include, but are not limited to neurofibromatosis.

The term "substantial lysis" means at least 10% of the proliferating cells are lysed, more preferably of at least 50% and most preferably of at least 75% of the cells are lysed. The percentage of lysis can be determined for tumor cells by measuring the reduction in the size of the tumor in the mammal or the lysis of the tumor cells in vitro.

A "mammal suspected of having a proliferative disorder" means that the mammal may have a proliferative disorder or tumor or has been diagnosed with a proliferative disorder or tumor or has been previously diagnosed with a proliferative disorder or tumor, the tumor or substantially all of the tumor has been surgically removed and the mammal is suspected of harboring some residual tumor cells.

Many of these proliferative disorders result from mutations in the ras proto-oncogene. However, as described above, proliferative disorders may also result from mutations in downstream effectors of ras. The instant invention contemplates the administration of reovirus to cells that are permissive to reovirus infection as a result of mutations in the downstream ral pathway.

The practitioner will understand that for the purposes of the instant disclosure, "ras" or "Ras" refer to the Ras gene or the Ras polypeptide as appropriate in context. "Ral," or "ral" refer to the ral gene or Ral polypeptide as appropriate in context. "RalGEF," or "ralGEF" refer to the RalGEF (guanine nucleotide exchange factor) gene or RalGEF polypeptide as appropriate in context. No limitations of the scope of the invention should be construed based on the particular use of these designations. Unless otherwise specified, the terms "ral pathway" and "Ral pathway" refer to all members of the ral signal transduction pathway, including ral and ralGEF genes and polypeptides, all genes and polypeptides that can result in activation of Ral or RalGEF (i.e., upstream elements of the ral pathway), and all genes and polypeptides that can be activated due to activation of Ral or RalGEF (i.e., downstream elements of the ral pathway). The term "ral-mediated proliferative disorder" refers to a cell proliferative disorder that results from activation of the ral pathway. The ral-mediated proliferative disorder may involve, for example, mutations of ral, ralGEF, or any element upstream or downstream of ral.

Activation of ras causes activation of the ral pathway. In other words, ras is an upstream element in the ral pathway. Thus, all the upstream elements in the ras pathway are also upstream elements in the ral pathway. It should be noted, however, that factors not in the ras pathway can also activate the ral pathway. Proliferative disorders resulting from activation or mutation of these other factors are also contemplated in the present invention. In particular, the present invention can be applied to the ral-mediated proliferative disorders that do not result from mutations in the ras gene or any element upstream of ras in the ras pathway.

Ral-mediated neoplasms are also susceptible to treatment by the methods of the invention. Such neoplasms may include, for example, forms of breast cancer, central nervous system cancer (e.g., neuroblastoma and glioblastoma), peripheral nervous system cancer, lung cancer, prostate cancer, colorectal cancer, thyroid cancer, renal cancer, adrenal cancer, liver cancer, lymphoma, and leukemia. Of particular interest are forms of cancer in which ras mutations are rare, for example, lymphoid malignancies, including diffuse large B-cell lymphomas) [Nedergaard et al. (1997) and references within].

"Administration to a proliferating cell or neoplasm" indicates that the reovirus is administered in a manner so that it contacts the proliferating cells or cells of the neoplasm (also referred to herein as "neoplastic cells"). The route by which the reovirus is administered, as well as the formulation, carrier or vehicle, will depend on the location as well as the type of the neoplasm. A wide variety of administration routes can be employed. For example, for a solid neoplasm that is accessible, the reovirus can be administered by injection directly to the neoplasm. For a hematopoietic neoplasm, for example, the reovirus can be administered intravenously or intravascularly. For neoplasms that are not easily accessible within the body, such as metastases or brain tumors, the reovirus is administered in a manner such that it can be transported systemically through the body of the mammal and thereby reach the neoplasm (e.g., intrathecally, intravenously or intramuscularly). Alternatively, the reovirus can be administered directly to a single solid neoplasm, where it then is carried systemically through the body to metastases. The reovirus can also be administered subcutaneously, intraperitoneally, topically (e.g., for melanoma), orally (e.g., for oral or esophageal neoplasm), rectally (e.g., for colorectal neoplasm), vaginally (e.g., for cervical or vaginal neoplasm), nasally or by inhalation spray (e.g., for lung neoplasm).

Reovirus can be administered systemically to mammals which are immune compromised or which have not developed immunity to the reovirus epitopes. In such cases, reovirus administered systemically, i.e., by intravenous injection, will contact the proliferating cells, resulting in lysis of the cells.

Immunocompetent mammals previously exposed to a reovirus subtype may have developed humoral and/or cellular immunity to that reovirus subtype. Nevertheless, it has been found that direct injection of the reovirus into a solid tumor in immunocompetent mammals will result in the lysis of the neoplastic cells.

On the other hand, when the reovirus is administered systemically to immunocompetent mammals, the mammals may produce an immune response to the reovirus. Although systemic administration of reovirus has been shown to successfully lead to oncolysis of local tumors in immunocompetent animals, it is preferable to avoid immune responses against reovirus, particularly in animals that have previously received large amounts of reovirus. Immune responses may be avoided if the reovirus is of a subtype to which the mammal has not developed immunity, or the reovirus has been modified as previously described herein such that it is immunoprotected, for example, by protease digestion of the outer capsid or packaging in a micelle.

Alternatively, it is contemplated that the immunocompetency of the mammal against the reovirus may be suppressed either by the co-administration of pharmaceuticals known in the art to suppress the immune system in general [Cuff et al. (1998)] or alternatively the administration of anti-antireovirus antibodies. The humoral immunity of the mammal against reovirus may also be temporarily reduced or suppressed by plasmaphoresis of the mammals blood to remove the anti-reovirus antibodies. The humoral immunity of the mammal against reovirus may additionally be temporarily reduced or suppressed by the intraveneous administration of non-specific immunoglobulin to the mammal.

It is contemplated that the reovirus may be administered to immunocompetent mammals in conjunction with the administration of immunosuppressants and/or immunoinhibitors. Such immunosuppressants and immunoinhibitors are known to those of skill in the art and include such agents as cyclosporin, rapamycin, tacrolimus, mycophenolic acid, azathioprine and their analogs, and the like. Other agents are known to have immunosuppressant properties as well (see, e.g., Goodman and Gilman, $7^{th}$ Edition, page 1242, the disclosure of which is incorporated herein by reference).

Such immunoinhibitors also include "anti-antireovirus antibodies," which are antibodies directed against anti-reovirus antibodies. Such antibodies can be made by methods known in the art. See for example "Antibodies: A laboratory manual" E. Harlow and D. Lane, Cold Spring Harbor Laboratory (1988). Such anti-antireovirus antibodies may be administered prior to, at the same time or shortly after the administration of the reovirus. Preferably an effective amount of the anti-antireovirus antibodies are administered in sufficient time to reduce or eliminate an immune response by the mammal to the administered reovirus. The terms "immunosuppressant" or "immune suppressive agent" include conventional immunosuppressants, immunoinhibitors, antibodies, and conditions such as radiation therapy or HIV infection which result in compromise of the immune system.

Alternatively or in addition, T cells and/or B cells, or subsets thereof, can be selectively removed from the animal, for example by administration of anti-CD4 and/or anit-CD8 antibodies.

This invention also includes pharmaceutical compositions which contain, as the active ingredient, one or more of the reoviruses associated with pharmaceutically acceptable carriers or excipients. The invention further includes pharmaceutical compositions which contain, as the active ingredient, one or more of the reoviruses, along with an appropriate immunosuppresant, associated with pharmaceutically acceptable carriers or excipients. In making the compositions of this invention, the active ingredient/reovirus is usually mixed with an excipient, diluted by an excipient or enclosed within such a carrier which can be in the form of a capsule, sachet, paper or other container. When the pharmaceutically acceptable excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

For preparing solid compositions such as tablets, the principal active ingredient/reovirus is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described herein. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices which deliver the formulation in an appropriate manner.

Another preferred formulation employed in the methods of the present invention employs transdermal delivery devices ("patches"). Such transdermal patches may be used to provide continuous or discontinuous infusion of the reovirus of the present invention in controlled amounts. The construction and use of transdermal patches for the delivery of pharmaceutical agents is well known in the art.. See, e.g., U.S. Pat. No. 5,023,252, herein incorporated by reference. Such patches may be constructed for continuous, pulsatile, or on demand delivery of pharmaceutical agents.

Other suitable formulations for use in the present invention can be found in *Remington's Pharmaceutical Sciences.*

The reovirus or the pharmaceutical composition comprising the reovirus may be packaged into convenient kits providing the necessary materials packaged into suitable containers. It is contemplated the kits may also include chemotherapeutic agents and/or anti-antireovirus antibody.

The reovirus is administered in an amount that is sufficient to treat the proliferative disorder (e.g., an "effective amount"). A proliferative disorder is "treated" when administration of reovirus to the proliferating cells effects lysis of the proliferating cells. This may result in a reduction in size of the neoplasm, or in a complete elimination of the neoplasm. The reduction in size of the neoplasm, or elimination of the neoplasm, is generally caused by lysis of neoplastic cells ("oncolysis") by the reovirus. Preferably the effective amount is that amount able to inhibit tumor cell growth. Preferably the effective amount is from about 1.0 pfu/kg body weight to about $10^{15}$ pfu/kg body weight, more preferably from about $10^2$ pfu/kg body weight to about $10^{13}$ pfu/kg body weight. For example, for treatment of a human, approximately $10^2$ to $10^{17}$ plaque forming units (PFU) of reovirus can be used, depending on the type, size and number of tumors present. The effective amount will be determined on an individual basis and may be based, at least in part, on consideration of the type of reovirus; the chosen route of administration; the individual's size, age, gender; the severity of the patient's symptoms; the size and other characteristics of the neoplasm; and the like. The course of therapy may last from several days to several months or until diminution of the disease is achieved.

The reovirus can be administered in a single dose, or multiple doses (i.e., more than one dose). The multiple doses can be administered concurrently, or consecutively (e.g., over a period of days or weeks). The reovirus can also be administered to more than one neoplasm in the same individual.

The compositions are preferably formulated in a unit dosage form, each dosage containing from about $10^2$ pfus to about $10^{13}$ pfu of the reovirus. The term "unit dosage forms" refers to physically discrete units suitable as unitary dosages for human subjects and other mammals, each unit containing a predetermined quantity of reovirus calculated to produce the desired therapeutic effect, in association with a suitable pharmaceutical excipient.

It has been found that the reovirus is effective for the treatment of solid neoplasms in immunocompetent mammals. Administration of unmodified reovirus directly to the neoplasm results in oncolysis of the neoplastic cells and reduction in the size of the tumor.

It is contemplated that the reovirus may be administered in conjunction with surgery or removal of the neoplasm. Therefore, provided herewith are methods for the treatment of a solid neoplasm comprising surgical removal of the neoplasm and administration of a reovirus at or near to the site of the neoplasm.

It is contemplated that the reovirus may be administered in conjunction with or in addition to radiation therapy.

It is further contemplated that the reovirus of the present invention may be administered in conjunction with or in addition to known anticancer compounds or chemotherapeutic agents. Chemotherapeutic agents are compounds which may inhibit the growth of tumors. Such agents, include, but are not limited to, 5-fluorouracil, mitomycin C, methotrexate, hydroxyurea, cyclophosphamide, dacarbazine, mitoxantrone, anthracyclins (Epirubicin and Doxurubicin), antibodies to receptors, such as herceptin, etopside, pregnasome, platinum compounds such as carboplatin; and cisplatin, taxanes such as taxol and taxotere, hormone therapies such as tamoxifen and anti-estrogens, interferons, aromatase inhibitors, progestational agents and LHRH analogs.

Preferably the reovirus is administered in the absence of 1,3-bis(2-chloroethyl)-1-nitrosourea (BCNU). For example, the 1,3-bis(2-chloroethyl)-1-nitrosourea (BCNU) is not administered to the mammal either before, during or after the mammal receives the reovirus.

The reovirus of the present invention have been found to reduce the growth of tumors that are metastatic. In an embodiment of the invention, a method is provided for reducing the growth of metastastic tumors in a mammal comprising administering an effective amount of a reovirus to the mammal.

Utility

The reoviruses of the present invention may be used for a variety of purposes. They may be used in methods for treating ral-mediated proliferative disorders in an animal. The reovirus may be used to reduce or eliminate neoplasms. They may be used in methods for treating metastases. They may be used in conjunction with known treatments for cancer including surgery, chemotherapy and radiation.

In order to further illustrate the present invention and advantages thereof, the following specific examples are given but are not meant to limit the scope of the claims in any way.

EXAMPLES

In the examples below, all temperatures are in degrees Celsius (unless otherwise indicated) and all percentages are weight percentages (also unless otherwise indicated).

In the examples below, the following abbreviations have the following meanings. If an abbreviation is not defined, it has its generally accepted meaning:

| | |
|---|---|
| μM = | micromolar |
| mM = | millimolar |
| M = | molar |
| ml = | milliliter |
| μl = | microliter |
| mg = | milligram |
| μg = | microgram |
| PAGE = | polyacrylamide gel electrophoresis |
| rpm = | revolutions per minute |
| FBS = | fetal bovine serum |
| DTT = | dithiothrietol |
| SDS = | sodium dodecyl sulfate |
| PBS = | phosphate buffered saline |
| DMEM = | Dulbecco's modified Eagle's medium |

-continued

| | |
|---|---|
| MEM = | modified Eagle's medium |
| β-ME = | β-mercaptoethanol |
| MOI = | multiplicity of infection |
| PFU or pfu = | plaque forming units |
| MAPK = | MAP kinase |
| phospho-MAPK = | phosphorylated-MAP kinase |
| HRP = | horseradish-peroxidase |
| PKR = | double-stranded RNA activated protein kinase |
| RT-PCR = | reverse transcriptase-polymerase chain reaction |
| GAPDH = | glyceraldehyde-3-phosphate dehydrogenase |
| EGFR = | epidermal growth factor receptors |
| MEK kinase = | mitogen-activated extracellular signal-regulated kinase |
| DMSO = | dimethylsulfoxide |
| SCID = | severe combined immunodeficiency |

Example 1

Use of Cells Harboring Ras Variants to Identify Downstream Effectors Associated with Reovirus Susceptibility To determine the downstream signaling events important for reovirus-mediated oncolysis, a panel of variant Ras-transformed-NIH-3T3 cells was assayed for susceptibility to reovirus infection. The panel comprised cells transformed with Ras variants harboring functionally distinct mutations in the effector-binding domain which causes selective interaction of the ras variants with only a subset of downstream ras effectors. Reovirus infections and assays for reovirus-replication were performed essentially as described in U.S. Pat. No. 6,136,307, incorporated by reference in its entirety.

The results of these experiments show that only cells transformed with RasV12G37, which retains the ability to activate RalGEFs while lacking the ability-to activate Raf or PI3-kinase, were susceptible to reovirus infection. These data suggest that RalGEF is the downstream effector responsible for the susceptibility of Ras-transformed cells to reovirus infection. The data further suggest that activation of the ral pathway, independent of the activation of other ras dowstream effectors, is necessary and sufficient to render cells susceptible to reovirus infection.

Example 2

Use of Cells Selectively Activated or Inhibited in the Ral Pathway to Confirm that Reovirus Susceptibility is Dependent Upon Activation of the Ral Pathway Rlf is an activated variant form of RalEGF. Cells transformed with Rlf were susceptible to reovirus infection, indicating that activation of the Ral pathway, independent of the activation of ras, results in reovirus susceptibility. In addition, selective inhibition of the Ral pathway rendered normally susceptible H-ras-containing cells reovirus-resistant. Taken together, these experiments provide convincing evidence that reovirus susceptibility is mediated by the Ral pathway. Reovirus infections and assays for reovirus replication were performed essentially as described in U.S. Pat. No. 6,136,307, incorporated by reference in its entirety.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A method of treating cells of a ral-mediated proliferative disorder, comprising contacting said cells with an effective amount of one or more reoviruses under conditions which result in substantial lysis of said cells, wherein said cells do not have mutations in the ras gene or in any element upstream of ras in the ras pathway.

2. The method of claim 1, wherein the reovirus is selected from the group consisting of a mammalian reovirus and an avian reovirus.

3. The method of claim 2, wherein the reovirus is a human reovirus.

4. The method of claim 3, wherein the reovirus is selected from the group consisting of serotype 1 reovirus, serotype 2 reovirus, and serotype 3 reovirus.

5. The method of claim 1, wherein the reovirus is a field isolate.

6. The method of claim 1, wherein more than one type of reovirus contacts the cells.

7. The method of claim 1, wherein more than one strain of reovirus contacts the cells.

8. The method of claim 1, wherein the reovirus is one or more recombinant reoviruses.

9. The method of claim 8, wherein the recombinant reovirus is generated by co-infection of mammalian cells with different subtypes of reovirus.

10. The method of claim 8, wherein the recombinant reovirus is naturally-occurring.

11. The method of claim 8, wherein the recombinant reovirus is non-naturally-occurring.

12. The method of claim 8, wherein more than one strain of recombinant reovirus contacts the cells.

13. The method of claim 8, wherein the recombinant reovirus is from two or more strains of reovirus.

14. The method of claim 13, wherein the two or more strains of reovirus are selected from the group consisting of strain Dearing, strain Abney, strain Jones, and strain Lang.

15. The method of claim 8, wherein the recombinant reovirus results from reassortment of reoviruses selected from the group consisting of serotype 1 reovirus, serotype 2 reovirus, and serotype 3 reovirus.

16. The method of claim 8, wherein two or more strains of recombinant reovirus contact the cells.

17. The method of claim 1, wherein the reovirus is one or more modified reoviruses.

18. The method of claim 17, wherein the reovirus is treated with a protease prior to contact.

19. The method of claim 1, wherein about 1 to about $10^{15}$ plaque forming units of reovirus/kg body weight contact the cells.

20. The method of claim 1, wherein the reovirus is contacted in a single dose.

21. The method of claim 1, wherein the reovirus is contacted in more than one dose.

22. The method of claim 1, wherein said cells of a ral-mediated proliferative disorder are from a neoplasm.

23. The method of claim 22, wherein the neoplasm is a solid neoplasm.

24. The method of claim 22, wherein the neoplasm is selected from the group consisting of lung cancer, prostate cancer, colorectal cancer, thyroid cancer, renal cancer, adrenal cancer, liver cancer, pancreatic cancer, breast cancer, and central and peripheral nervous system cancer.

25. The method of claim 22, wherein the neoplasm is a hematopoietic neoplasm.

26. The method of claim 22, wherein the neoplasm is metastatic.

27. The method of claim 1, wherein said cells of a ral-mediated proliferative disorder are from a neurofibromatosis.

28. The method of claim 1, wherein the reovirus is immunoprotected.

29. The method of claim 1, wherein the reovirus is encapsulated in a micelle.

30. The method of claim 1, wherein the reovirus is contacted along with an effective amount of an anti-antireovirus antibody.

31. The method of claim 1, further comprising contacting said cells of a ral-mediated proliferative disorder with an effective amount of a chemotherapeutic agent, with the proviso that the chemotherapeutic agent is not BCNU.

* * * * *